(12) United States Patent
Koay et al.

(10) Patent No.: US 11,213,329 B2
(45) Date of Patent: Jan. 4, 2022

(54) BONE FRACTURE FIXATION CLAMP

(71) Applicant: DePuy Synthes Products, Inc., Raynham, MA (US)

(72) Inventors: Kenny Koay, West Chester, PA (US); Peter Fatone, West Chester, PA (US); Timothy Reppert, Foster City, CA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 16/804,544

(22) Filed: Feb. 28, 2020

(65) Prior Publication Data
US 2021/0267655 A1 Sep. 2, 2021

(51) Int. Cl.
A61B 17/80 (2006.01)
A61B 17/82 (2006.01)
(Continued)

(52) U.S. Cl.
CPC ........ *A61B 17/8061* (2013.01); *A61B 17/809* (2013.01); *A61B 17/8019* (2013.01);
(Continued)

(58) Field of Classification Search
CPC . A61B 17/28; A61B 17/282; A61B 2017/681; A61B 17/8004; A61B 17/8019;
(Continued)

(56) References Cited

U.S. PATENT DOCUMENTS 5,085,660 A * 2/1992 Lin ..................... A61B 17/8057
606/288
5,662,443 A * 9/1997 Dziaba .................. F16B 39/286
411/280
(Continued)

FOREIGN PATENT DOCUMENTS

EP 997107 A2 * 3/2000
EP 1889574 A2 2/2008

OTHER PUBLICATIONS

Roosen et al., "Dorsal Spondylodesis of the Upper Cervical Spine—a New Technical Concept", Medizinisch Orthopadische Technik, vol. 103, No. 1, 1983, Stuttgart, Germany, pp. 18-21.**.

*Primary Examiner* — Matthew J Lawson
(74) *Attorney, Agent, or Firm* — Fay Kaplun & Marcin, LLP

(57) ABSTRACT

A bone fixation clamp includes first and second clamp members, a stud, and a locking nut. The first member extends along a curve corresponding to an outer surface of a first portion of bone and includes an opening extending therethrough along an axis extending adjacent to the bone. The second member extends along a curve corresponding to an outer surface of a second portion of bone. The stud is receivable within the opening of the first member. The nut includes a threaded channel threadedly engaging a portion of the stud so that, when the first and second members are in the operative configuration, the nut is threadable over the stud to fix the first and second members over bone. The nut includes an anti-loosening feature which, when the nut is (Continued)

threaded over the stud, results in an interference with threading along the stud.

22 Claims, 7 Drawing Sheets

(51) Int. Cl.
*A61B 17/86* (2006.01)
*A61B 17/68* (2006.01)

(52) U.S. Cl.
CPC .......... *A61B 17/82* (2013.01); *A61B 17/8665* (2013.01); *A61B 2017/681* (2013.01); *A61B 2017/867* (2013.01)

(58) Field of Classification Search
CPC ............ A61B 17/8052; A61B 17/8057; A61B 17/8061; A61B 17/808; A61B 17/809; A61B 17/82; A61B 2017/867; F16B 39/286
See application file for complete search history.

(56) References Cited

U.S. PATENT DOCUMENTS

| | | | |
|---|---|---|---|
| 9,999,456 B2* | 6/2018 | Powell | A61B 17/84 |
| 10,835,301 B1* | 11/2020 | Paranjpe | A61B 17/8009 |
| 2012/0290017 A1 | 11/2012 | Haidukewych | |
| 2018/0132909 A1 | 5/2018 | Hackathorn, II | |
| 2019/0142485 A1* | 5/2019 | Garcia | A61B 17/8057 606/291 |
| 2019/0159819 A1* | 5/2019 | Fatone | A61B 17/80 |
| 2019/0183549 A1* | 6/2019 | Singh | A61B 17/8061 |

* cited by examiner

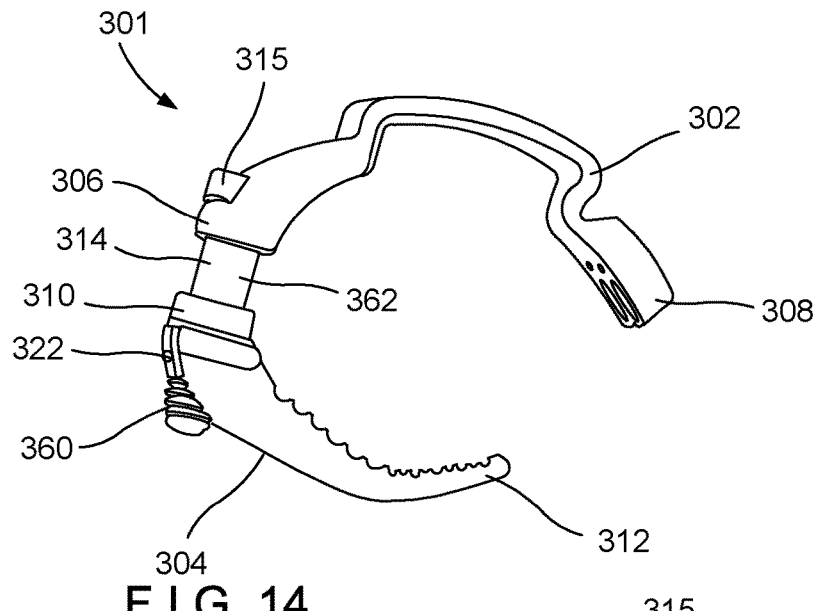
FIG. 14
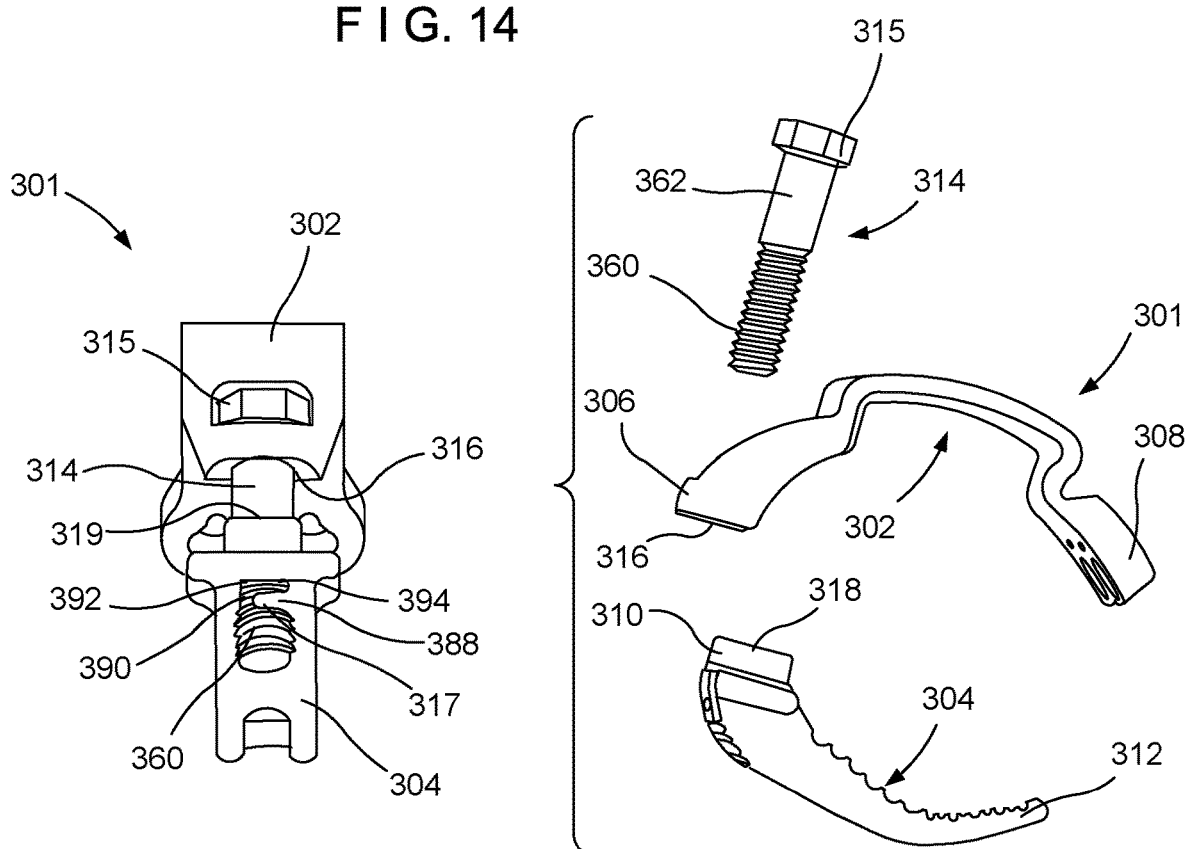
FIG. 15
FIG. 16

BONE FRACTURE FIXATION CLAMP

BACKGROUND

Periprosthetic fractures—fractures around areas of bone that have been previously fitted with a metal prosthesis—are, in some cases, difficult to treat because the previously implanted metal prosthesis (e.g., intramedullary nails, hip replacement implants) may preclude the use of bone fixation devices that extend into certain portions the bone. Such bone fixation procedures therefore use a combination of fixation devices such as, for example, clamps and compression plates.

SUMMARY OF THE INVENTION

The present disclosure relates to a bone fixation clamp includes first and second clamp members, a stud, and a locking nut. The first clamp member extends from a first end to a second end along a curve corresponding to an outer surface along a first target portion of a bone. The first end includes an opening extending therethrough along an axis which, when the first clamp member is positioned along the first target portion in an operative configuration, extends adjacent to the bone. The second clamp member extends from a first end to a second end along a curve corresponding to an outer surface along a second target portion of the bone. The stud extends longitudinally from the first end of the second clamp member to a free end so that, when the second clamp member is positioned along the second target portion of the bone in the operative configuration, the stud is receivable within the opening of the first clamp member along the axis of the opening. The locking nut includes a threaded channel configured to threadedly engage a portion of the stud so that, when the first and second clamp members are in the operative configuration, the locking nut is threadable over the stud to fix the first and second clamp members over the bone, the locking nut including an anti-loosening feature which, when the locking nut is threaded over the stud, results in an interference with threading along the stud.

In an embodiment, the anti-loosening feature includes a deformable portion deforming to interfere with threading along the stud.

In an embodiment, the locking nut extends longitudinally from a first end to a second end, the locking nut including a pair of grooves extending into the first end, through a wall of the locking nut so that the threaded channel is open to an exterior of the locking nut via the pair of grooves.

In an embodiment, the pair of grooves are substantially diametrically positioned relative to one another.

In an embodiment, the deformable portion is defined via a first slit extending through the wall of the locking nut from a first one of the pair of grooves about a portion of a circumference of the locking nut and a second slit extending through the wall of the locking nut from an end of the first slit toward a the first end of the locking nut.

In an embodiment, the anti-loosening feature includes a reduced minor diameter along a first portion of the threaded channel relative to a minor diameter along a second portion of the threaded channel.

In an embodiment, the stud and the opening of the first clamp member are correspondingly sized and shaped so that the stud is non-rotatably receivable within the opening.

In an embodiment, the stud includes a flat along a length thereof and the opening of the first clamp member includes a corresponding flat surface therealong.

In an embodiment, a length of the stud is selected to correspond to a width of a bone being treated.

In an embodiment, the second clamp member includes an elongated slot extending therealong and therethrough from a bone-facing surface of the second clamp member which, when the second clamp member is in the operative configuration faces toward a bone, to a surface of the second clamp member opposing the bone-facing surface of the second clamp member.

In an embodiment, the elongated slot is open at the second end of the second clamp member to define a pair of prongs of the second clamp member.

In an embodiment, the second clamp member includes a connecting web connecting the pair of prongs along a portion of the elongated slot.

In an embodiment, the first clamp member includes a groove extending therealong, the groove sized and shaped to correspond to a bone plate so that, the first clamp member is mountable over a portion of a bone along which a bone plate is positioned.

In an embodiment, a portion of the first clamp member including the groove includes a connecting opening extending therethrough so that, when the connecting opening is aligned with a corresponding hole of a bone plate over which the first clamp member is mounted, a screw is insertable through the connecting opening and the hole of the plate to fix the first clamp member and the bone plate relative to one another.

The present disclosure also relates to a bone fixation system which includes a clamp, a locking nut, and an insertion device. The clamp includes a first clamp member and a second clamp member, the extending from a first end to a second end along a curve corresponding to an outer surface along a lateral side of a bone, the first end including an opening extending therethrough along an axis which, when the first clamp is positioned along the bone in an operative configuration, extends adjacent to the bone, the second clamp member extending from a first end to a second end along a curve corresponding to an outer surface along a medial side of the bone, a stud extending longitudinally from the first end of the second clamp member to a free end so that, when the second clamp member is positioned along the second target portion of the bone in the operative configuration, the stud is receivable within the opening of the first clamp member along the axis of the opening, the stud including a channel at the free end thereof.

The locking nut includes a threaded channel configured to threadedly engage a portion of the stud so that, when the first and second clamp members are in the operative configuration, the locking nut is threadable over the stud to fix the first and second clamp members over the hone, the locking nut including an anti-loosening feature which, when the locking nut is threaded over the stud, results in an interference with threading along the stud.

The insertion device includes a sleeve extending from a proximal end to a distal end and sized and shaped to be slidable insertable through the threaded channel of the locking nut and the opening of the first clamp member, the distal end configured to engage the recess of the stud and the proximal end configured to engage the opening of the first clamp member so that, when the distal end of the sleeve engages the stud and the proximal end of the sleeve engages the first clamp member, second ends of the first and second clamp members are separated from one another by a distance greater than a width of the bone so that the fixation clamp is positionable about the bone.

In an embodiment, the channel of the stud includes a recess extending along a portion thereof.

In an embodiment, the distal end of the sleeve includes a plurality of fingers, one of the fingers including a protrusion extending laterally therefrom, the protrusion configured to be received within the recess of the stud so that the distal end of the sleeve engages the channel of the stud via a snap fit.

In an embodiment, the insertion device includes a rod longitudinally slidable within the sleeve, the rod movable between a locking position, in which the rod is received between the fingers to lock the protrusion within the recess and the sleeve relative to the second clamp member, and an unlocked configuration, in which the rod is moved proximally relative to the sleeve so that the fingers are permitted to mov radially inward relative to one another to disengage the sleeve from the channel of the stud.

In an embodiment, the proximal end of the sleeve includes a stop for engaging the first clamp member.

In an embodiment, the anti-loosening feature includes a deformable portion deforming to interfere with threading along the stud, the deformable portion defined via slits extending through a wall of the locking nut.

In an embodiment, the anti-loosening feature includes a reduced minor diameter along a first portion of the threaded channel relative to a minor diameter along a second portion of the threaded channel.

In addition, the present disclosure relates to a bone fixation clamp which includes a first clamp member, a second clamp member, and a shoulder bolt. The first clamp member extends from a first end to a second end along a curve corresponding to an outer surface along a first target portion of a bone, the first end including a first opening extending therethrough along an axis which, when the first clamp is positioned along the first target portion in an operative configuration, extends adjacent to the bone.

The second clamp member extendes from a first end to a second end along a curve corresponding to an outer surface along a second target portion of the bone, the first end of the second clamp member including a second opening extending therethrough along an axis so that, in the operative configuration, axes of the first and second openings are substantially coaxially aligned, the second opening including a threading therealong, the second opening including a deformable portion; and The shoulder bolt is configured to fix the first and second clamp members relative to one another over a bone, the shoulder bolt including a shoulder and a shaft sized and shaped to be slidably inserted through the first opening, a portion of the shaft including a threading for engaging the thread of the second opening, the deformable portion deforming to interfere with the threading of the shaft.

In an embodiment, a threaded portion of the shaft of the shoulder bolt is connected to the shoulder via an unthreaded portion.

In an embodiment, the deformable portion is defined via slits extending through a wall of the second opening.

In an embodiment, the shoulder is configured to engage a portion of the first opening so that, when the shoulder abuts the first opening and the shoulder bolt is tightened relative to the second clamp member, the first and second clamp members are drawn toward one another.

BRIEF DESCRIPTION OF THE DRAWINGS

FIG. 14 shows a side view of a fixation clamp according to another exemplary embodiment of the present disclosure;

FIG. 15 shows an exploded side view of the fixation clamp of FIG. 14; and

FIG. 16 shows another side view of the fixation clamp, rotated ninety degrees relative to the fixation clamp shown in FIG. 14.

DETAILED DESCRIPTION

Figure 1:
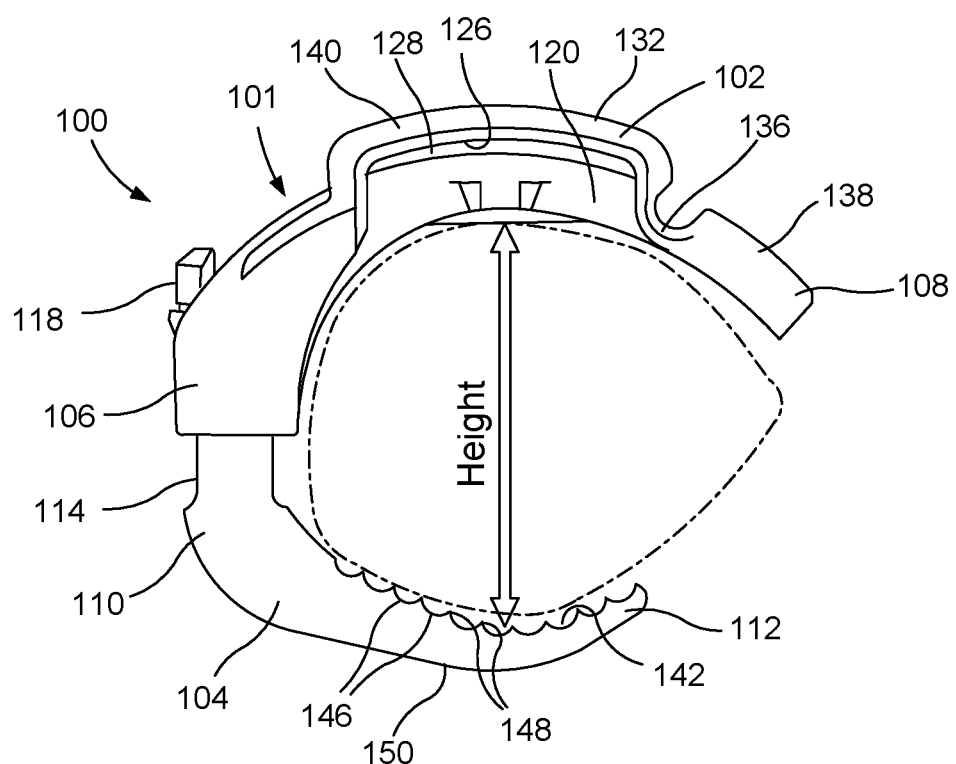
FIG. 1 shows a side view of a fixation system according to an exemplary embodiment of the present disclosure.

The present invention may be further understood with reference to the following description and the appended drawings, wherein like elements are referred to with the same reference numerals. The present invention relates to the treatment of fractured bones and, in particular, relates to a system and method for stabilizing a fractured or otherwise damaged bone by securing a bone fixation device to an outer surface thereof. The exemplary embodiments describe a fixation system comprising a fixation clamp which, in one embodiment, may be used in conjunction with other fixation devices such as, for example, a bone plate, to treat periprosthetic fractures of a long bone.

The exemplary fixation clamp is comprised of a first clamp member and a second clamp member configured to be coupled to one another so that, when coupled, the fixation clamp is mounted over the bone plate and extends about a periphery of the bone to provide stability and/or support to the bone. In one embodiment, the first and second clamp members are coupled when the first clamp member a stud of the second clamp member is received within an opening of the first clamp member and a locking nut is threaded over the stud so that the first and second clamp members are fixed relative thereto. The locking nut includes an anti-loosening feature preventing post-operative loosening thereof. In particular, the locking nut is plastically deformable, such that when the locking nut is threaded over the stud, the locking nut elastically deforms and maintains tension on the threads, thus creating an interference with threads of the stud to lock the nut relative thereto. It will be understood by those of skill in the art that the fixation clamp described herein may be used in conjunction with any of a variety of fixation devices to treat any of a variety of bones.

As shown in FIGS. 1-11, a fixation system 100 according to an exemplary embodiment of the present disclosure comprises a fixation clamp 101 including a first clamp member 102 and a second clamp member 104 couplable to one another so that, when coupled to one another in an operative configuration, the fixation clamp 101 extends about a portion of a periphery of a long bone to stabilize, for example, a Periprosthetic fracture. It will be understood by those of skill in the art that the fixation clamp 101 may be used in conjunction with other bone fixation devices such as, for example, a bone plate 120 configured to be positioned along a portion of a length of the bone.

In one embodiment, the first clamp member 102 extends from a first end 106 to a second end 108 along a curve substantially corresponding to a curve of a portion of an outer surface of a portion of bone on which the clamp is to be positioned. The second member 104 also extends from a first end 110 to a second end 112 along a curve substantially corresponding to an outer surface a portion of the bone it is to contact when positioned as desired. The first ends 106, 110 of the first and second clamp members 102, 104 are configured to be coupled to one another so that, in the operative configuration, the coupled first and second clamp members 102, 104 to one another to extend about a portion of a periphery of the bone. In one embodiment, the first end 106 of the first clamp member 102 includes an opening 116 extending therethrough.

The opening 116 is sized, shaped and configured to receive a stud 114 extending from the first end 110 of the second member 104 through the opening 116 to couple the first and second clamp members 102, 104 to one another. A locking nut 118 including an anti-loosening feature 122 is configured to be threaded over an end of the stud 114 to lock the first and second clamp members 102, 104 relative to one another. The fixation system 100 also comprises an insertion device 124 which hold the first and second clamp members 102, 104 relative to one another to facilitate insertion of the fixation clamp 101 into a desired position about the bone.

Figure 2:
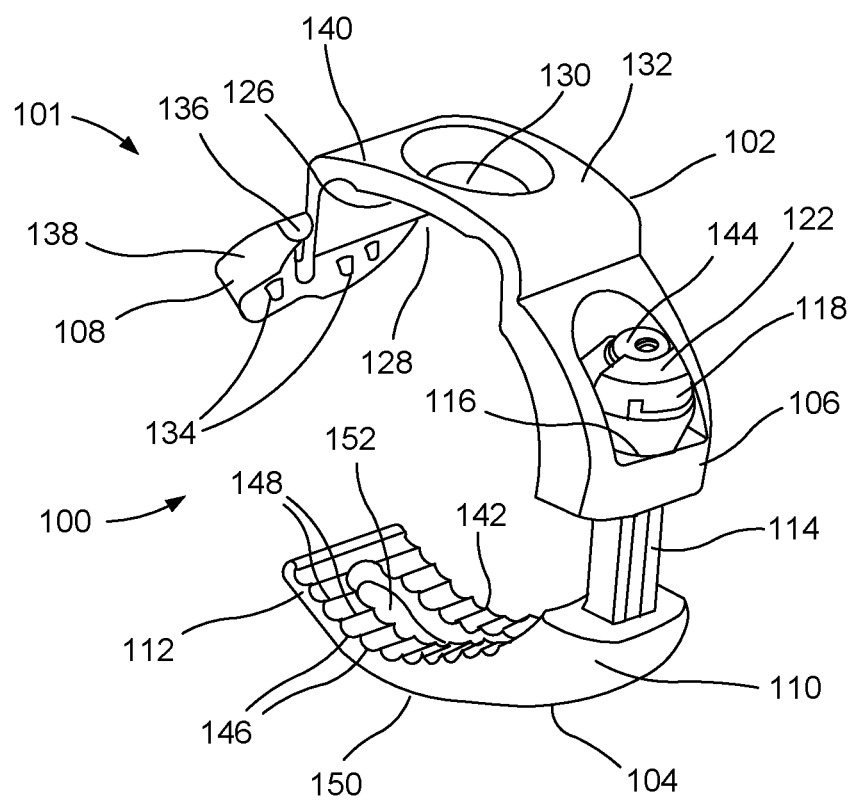
FIG. 2 shows a perspective view of a fixation clamp according to the system of FIG. 1.

As described above, the fixation clamp 101 includes the first and second clamp members 102, 104 coupled to one another via the stud 114 and locking nut 118. As shown in FIG. 2, the first clamp member 102 extends from the first end 106 to the second end 108 and has curve that corresponds to, for example, a portion of a surface of a lateral portion of the bone. In particular, in one embodiment, a bone-facing surface 126 of the first clamp member 102 is configured to extend, in the operative configuration, about a portion of a lateral surface of the bone. The first clamp member 102 may also include a recess 128 along the bone-facing surface 126 sized and shaped to correspond to the bone plate 120 so that the first clamp member 102 is mountable over the bone plate 120 in the operative configuration.

The first clamp member 102 also includes a connection screw hole 130 extending through the first clamp member 102 from a surface 132 which, in the operative configuration faces away from the bone, to the bone-facing surface 126. The connection screw hole 130 extends through a portion of the first clamp member along which the recess 128 extends so that, when the first clamp member 102 is mounted over the bone plate 120, a connection screw is insertable through the connection screw hole 130 to interface with and engage a screw-receiving opening of the bone plate 120. A connection screw through the connection screw hole 130 therefore fixes the fixation clamp 101 relative to the bone plate 120 and/or the bone.

In one embodiment, the first clamp member 102 also includes a pair of bone fixation element receiving holes 134. Each of the bone fixation element receiving holes 134 extends along an axis from the surface 132 to the bone-facing surface 126 and is configured to receive a bone fixation element (e.g., a bone screw) therein to fix the first clamp member 102 relative to the bone. Each of the bone fixation element receiving holes 134 extends through a portion 138 of the first clamp member 102 at the second end 108 and is connected to a remaining portion 140 of the first clamp member 102 via a bending zone 136. In one embodiment, the bending zone 136 is defined via a reduced thickness of the first clamp member 102 at the bending zone.

In particular, a distance between the surface 132 and the bone facing surface 126 at the bending zone 136 is reduced relative to a thickness of the first clamp member 102 along other portions thereof so that the portion 138 of the first clamp member 102 including the bone fixation element holes 134 is bendable relative to the remaining portion 140 of the first clamp member 102 to specifically configure a shape of the first clamp member 102 to a target portion of the bone.

As would be understood by those skilled in the art, the bone fixation element receiving holes 134 may be configured to receive any of a variety of different types of bone screws. For example, in one embodiment, one or more of the bone fixation element receiving holes 134 may be a variable angle hole configured to receive a variable angle screw therein at a user-selected angle within a predetermined range of permitted angulations relative to the axis of the bone fixation element receiving hole 134.

In another example, one or more of the bone fixation element receiving holes may be a locking hole including threading along an interior surface thereof configured to engaging corresponding threading on the head of a bone screw. It will be understood by those of skill in the art that the bone fixation element receiving holes 134 may have any of a variety of configurations so long as the bone fixation element receiving holes 134 are configured to receive bone fixation elements (screws) therein. It will also be understood by those of skill in the art that although the exemplary embodiment shows and describes a pair of holes 134, the first clamp member 102 may have any number of bone fixation element receiving holes 134 (one or more) and each bone fixation element holes 134 may have a different configuration from another one of the holes 134.

As described above, the opening 116 extends through the first end 106 to connect the first end 106 of the first clamp member 102 to the first end 110 of the second clamp member 104. In particular, the opening 116 is sized, shaped and configured to receive the stud 114 of the second clamp member 104, as will be described in further detail below. The opening 116 extends along an axis which, when the first clamp member 102 is in the operative configuration extends along an exterior of the bone, adjacent to the bone so that a stud 114 inserted therein does not intersect the bone at any point. Generally, the axis of the opening 116 will not intersect the bone.

As shown in FIG. 2, the second clamp member 104 extends from the first end 110 to the second end 112 and has a curve that corresponds to, for example, a curve of a surface of a portion of a medial side of the bone. In particular, in one embodiment, a bone-facing surface 142 of the second clamp member 104 is configured to extend about a portion of a lateral surface of the bone, in the operative configuration. As described above, the second clamp member 104 includes the stud 114 extending from the first end 110 to a tree end 144 so that the stud 114 is receivable within the opening 116 of the first clamp member 102 to couple the first and second clamp members 102, 104 together.

Figure 3:
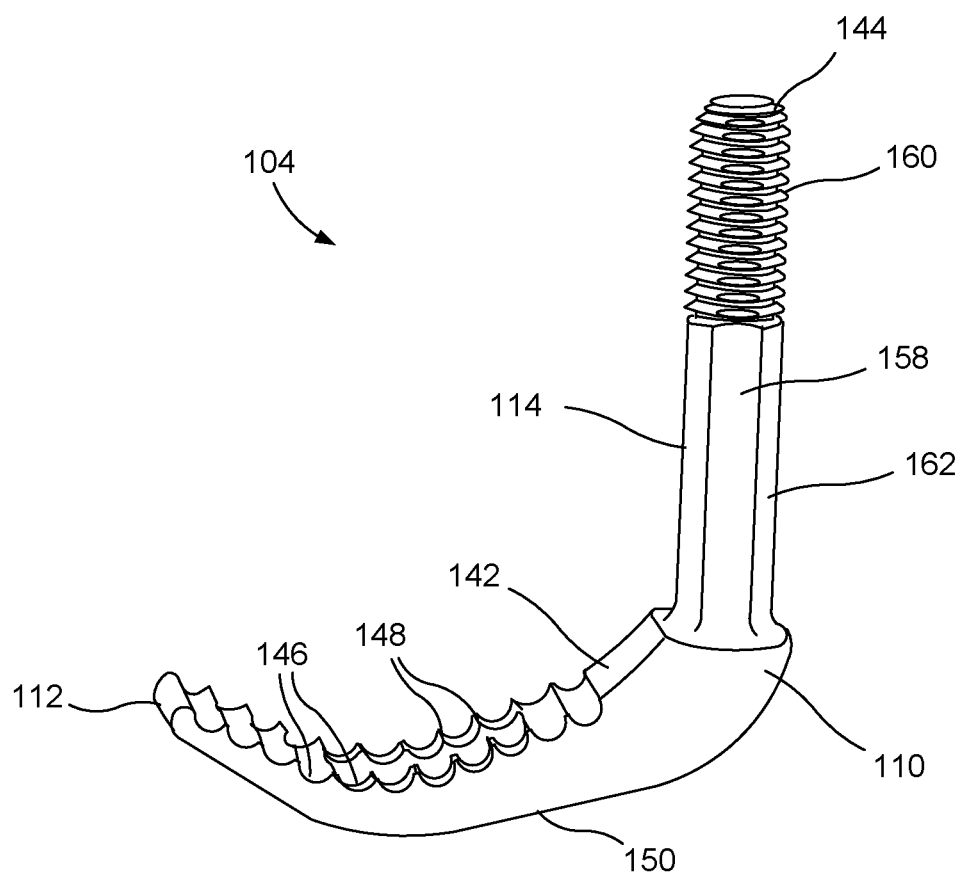
FIG. 3 shows a perspective view of a second clamp member of the fixation clamp according to the system of FIG. 1.
Figure 4:
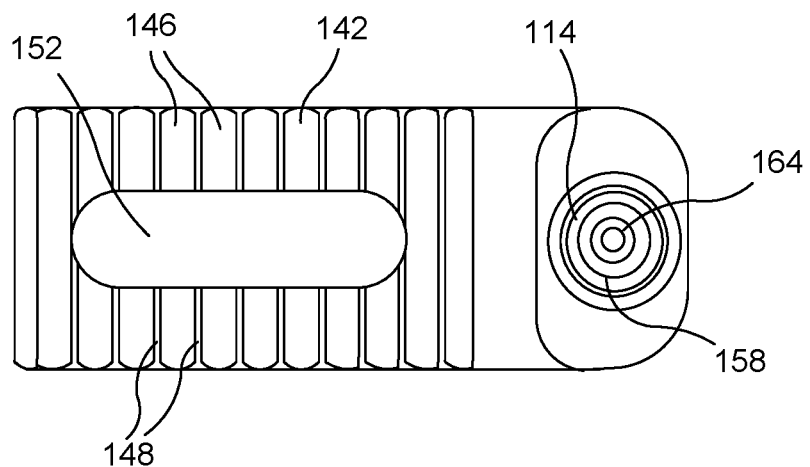
FIG. 4 shows a plan view of the second clamp member of FIG. 3.
Figure 5:
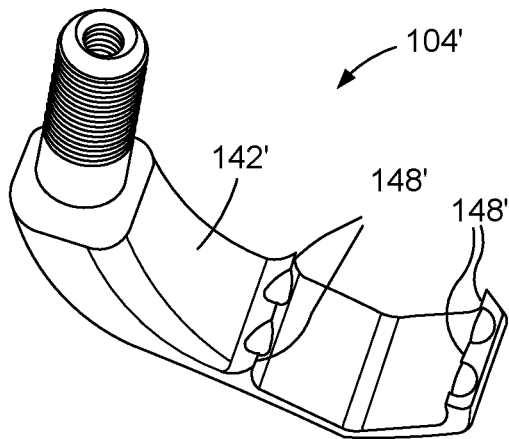
FIG. 5 shows a perspective view of a second clamp member according to an alternate embodiment.

In one embodiment, as shown in FIGS. 3-4, the bone-facing surface 142 includes a plurality of laterally extending grooves 146 to define gripping features 148 extending along a length of the bone-facing surface 142. In one embodiment, the gripping features 148 may be configured as ridges and/or teeth-like elements configured to improve a grip of the second clamp member 104 along the bone. It will be understood by those of skill in the art that a depth, size and configuration of the grooves 146 may be varied to define various gripping features having varying gripping structures. In another embodiment, as shown in FIG. 5, rather than grooves 146, a second clamp member 104' may include one or more sharp teeth 148' protruding from a bone-facing surface 142' to grip a bone received therealong.

In one embodiment, the second clamp member 104 also includes an elongated slot 152 extending therethrough from a surface 150 which, when the fixation clamp 101 is in the operative configuration faces away from the bone, to the bone-facing surface 142 along a length of the second clamp member 104. It will be understood by those of skill in the art that, if damage occurs, the slot 152 mitigates this damage to a periosteum of the bone by reducing an area of contact between the second clamp member 104 and surrounding soft tissue and blood vessels. In the embodiment shown in FIGS. 3 and 4, the elongated slot 152 is closed at the second end 110. In other words, the elongates slot 152 extends along a portion of a length of the second clamp member 104, but does not extend beyond either the first end 110 or the second end 112.

Figure 6:
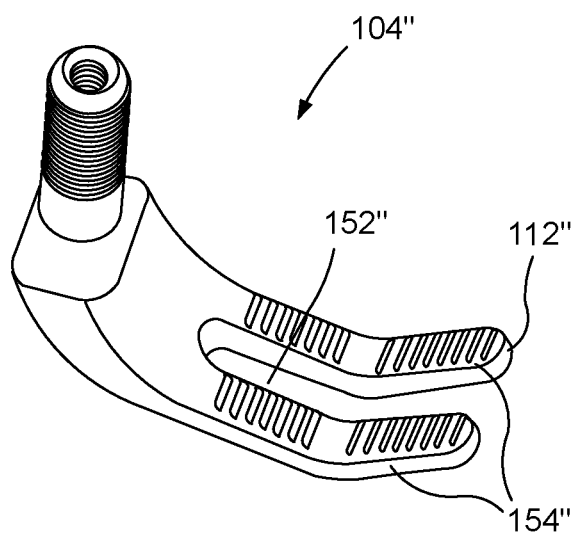
FIG. 6 shows a perspective view of a second clamp member according to another alternate embodiment.
Figure 7:
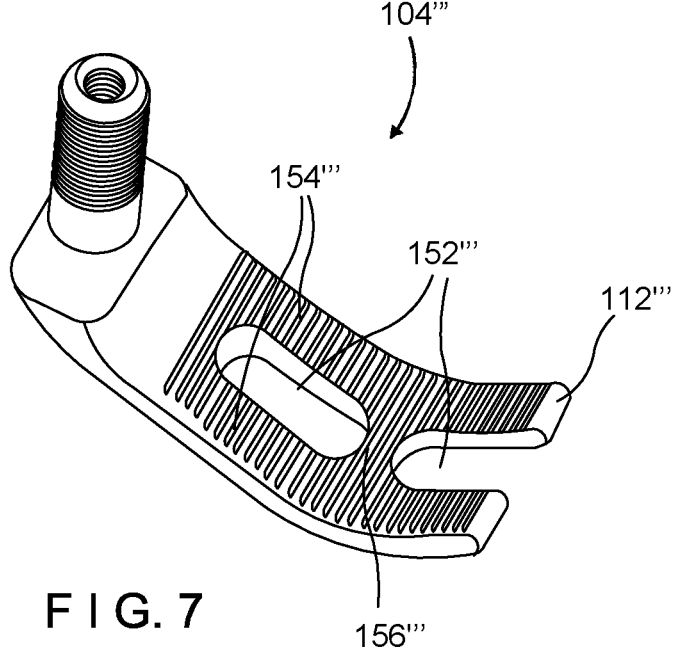
FIG. 7 shows a perspective view of a second clamp member according to yet another alternate embodiment.

It will be understood by those of skills in the art, however, that a configuration of the elongated may be varied. In another embodiment, as shown in FIG. 6, a second clamp member 104" includes an elongated slot 152" that is open at the second end 112" of the second clamp member 104" to define two prongs 154" of the second clamp member 104". The two prongs 154" may provide some flexibility when using a fixation clamp over a portion of a bone that has a varying diameter from a first point about which a first one of the prongs 154" is positioned and a second point about which a second one of the prongs 154" is positioned. In yet another example, as shown in FIG. 7, an elongated slot 152''' of a second clamp member 104''' is similarly open at a second end 112''' to define two prongs 154'''. The two prongs 154''', however, are connected to one another via a connecting web 156''' extending across the elongated slot 152'''. The connecting web 156''' may be positioned along any point along a length of the elongated slot 152'''.

The stud 114 extends from the first end 110 of the second clamp member 104 so that, when the first and second clamp members 102, 104 are in the operative configuration, the stud 114 is received within correspondingly sized and shaped opening 116 of the first clamp member 102 along the axis of the opening 116. In one embodiment, the stud 114 and the opening 116 may be keyed relative to one another so that the stud 114 is non-rotatably received within the opening 116. For example, the stud 114 may include a flat 158 extending along a length thereof for engaging a corresponding flat surface of the opening 116. The stud includes a threaded portion 160 along the free end 144. In one embodiment, the threaded portion 160 is connected to the first end 110 of the second clamp member 104 via an unthreaded portion 162. In this embodiment, the flat 158 extends along both the unthreaded portion 162 and threads of the threaded portion 160.

Figure 8:
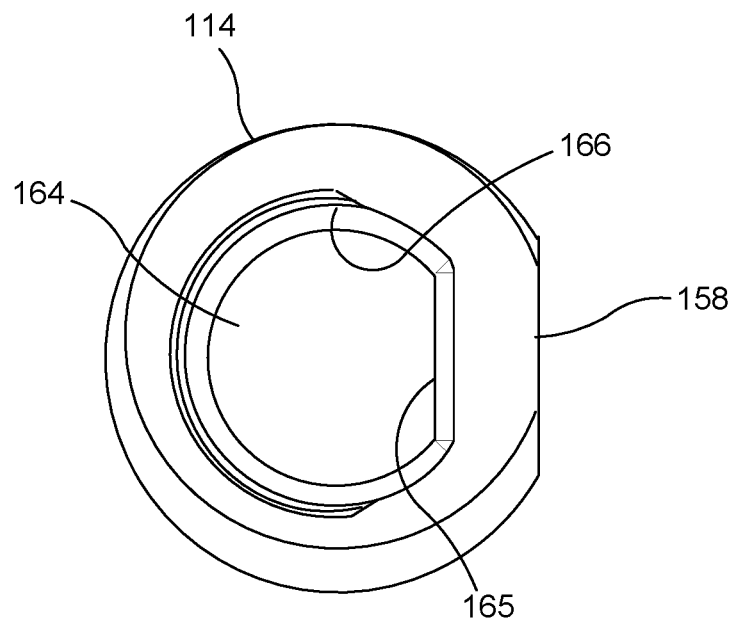
FIG. 8 shows plan view of a portion of a stud of the second clamp member of FIG. 3.
Figure 9:
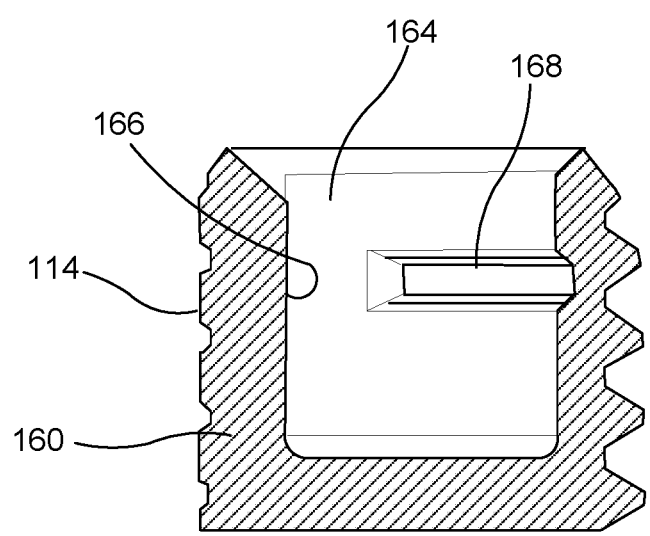
FIG. 9 shows a cross-sectional view of a portion of the stud of FIG. 8.

The stud 114 also includes a channel 164 extending into the free end 144 along a portion of a length thereof for receiving and engaging a portion of the insertion device 124. In one embodiment, as shown in FIG. 8, the channel 164 may also be keyed to the portion of the insertion device 124 to be received therein, including, for example, a flat 165 along a portion of a surface 166 of the channel 164. The flat 165 facilitates a non-rotatable engagement with the insertion device 124. In one embodiment, as shown in FIG. 9, the surface 166 of the channel 164 includes a recess 168 extending into a portion thereof for engaging a corresponding portion of the insertion device 124. As will be described in further detail below, the insertion device 124 may be inserted through the opening 116 of the first clamp member 102 to engage the channel 164 of the stud 114 to hold the first and second clamp members 102, 104 relative to one another so that a surgeon or other user does not inadvertently lose a grip on either the first clamp member 102 and/or the second clamp member 104 during insertion of the fixation clamp 101 over the bone.

Figure 10:
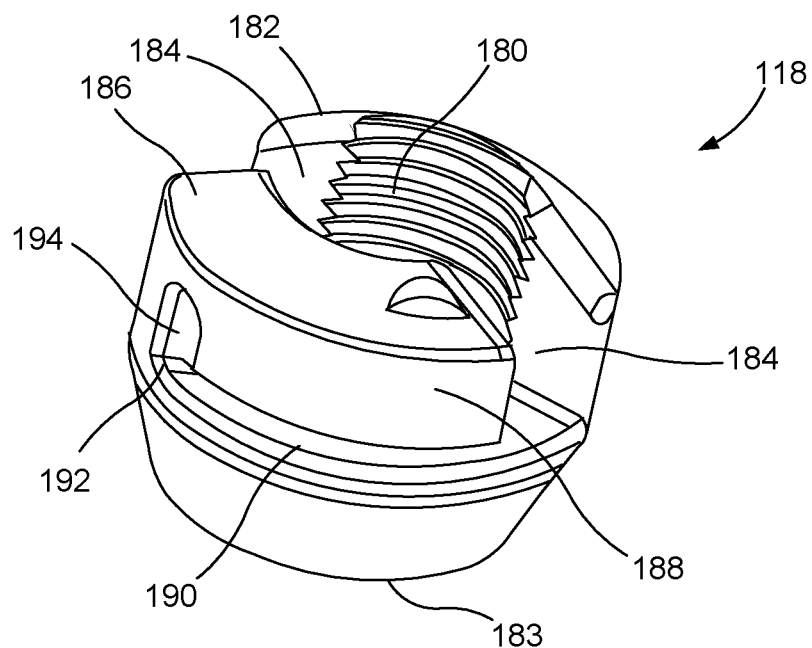
FIG. 10 shows a perspective view of a locking nut according to the system of FIG. 1.

As described above, the locking nut 118 is configured to be threaded over the stud 114. As shown in FIG. 10, the locking nut 118 includes a threaded channel 180 extending therethrough, the threaded channel 180 configured to engage the threaded portion 160 of the stud 114. Thus, when the fixation clamp 101 is positioned about the bone, the locking nut 118 may be tightened relative to the stud 114 (i.e., rotated about the threaded portion 160 of the stud 114) to draw the first and second clamp member 102, 104 toward one another so that the first and second clamp members 102, 104 are compressed over the bone and/or the bone plate 120. A surface 182 of the locking nut 118 which, in the operative configuration, faces away from the second clamp member 104, includes a pair of grooves 184 extending thereinto, through a wall 186 of the locking nut 118. In one embodiment, the pair of grooves 184 extend through portions of the locking nut 118 that are substantially diametrically opposed to one another.

As described above, the locking nut 118 includes an anti-loosening feature 122 so that, as the locking nut 118 is tightened, the locking nut 118 is locked relative to the stud 114 to prevent post-operative loosening of the nut 118. In one embodiment, the anti-loosening feature 122 includes a deformable portion 188 defined via a first slit 190 and a second slit 194 extending through the wall 186 of the locking nut 118. In particular, the first slit 190 extends through the wall 186 from a first one of the pair of grooves 184, so that the first slit 190 is open to the first one of the grooves 184, about a portion of a circumference of the locking nut 118 to an end 192 proximate, but not open to a second one of the pair of grooves 184. The second slit 194 extends from the end 192 of the first slit 190 toward the surface 182 of the locking nut 118 which, in the operative configuration, faces away from the second clamp member 104.

In one embodiment, the first slit 190 extends substantially midway between the surface 182 and an opposing surface 183. The first and second slits 190, 194 permit deformation of the deformable portion 188 toward the second clamp member 104, as the locking nut 118 is tightened about the stud 114. Such a deformation results in an interference between the locking nut 118 and the threaded portion 160, which locks the locking nut 118 thereover to prevent post-operative loosening. Although the exemplary embodiment shows and describes one deformable portion 188, it will be understood by those of skill in the art that the locking nut 118 may also include a second deformable portion extending along a substantially opposing portion of the locking nut 118.

Figure 11:
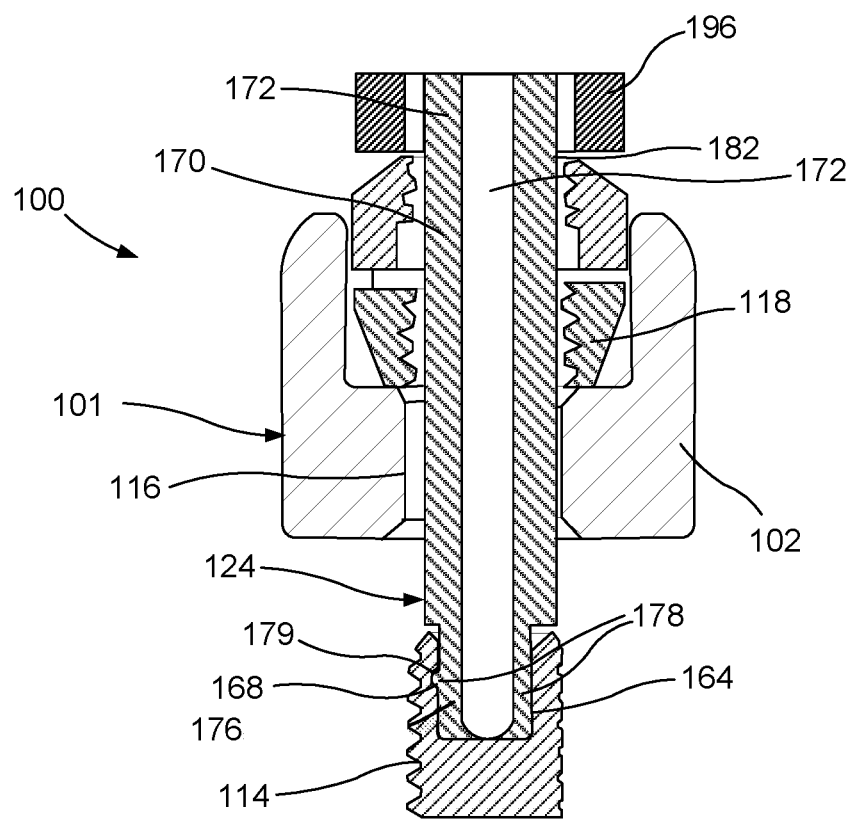
FIG. 11 shows a cross-sectional view of the system according to FIG. 1, including an insertion device.

In one embodiment, as shown in FIG. 11, the insertion device 124 includes a sleeve 170 and an elongated rod 172 longitudinally slidable therein. The sleeve 170 extends longitudinally from a proximal end 174 to a distal end 176 and is sized and shaped to be slidably inserted through both the threaded channel 180 of the locking nut 118 and the opening 116 of the first clamp member 102. The distal end 176 is sized and shaped to be received within the channel 164 at the free end 144 of the stud 114. In one embodiment, the distal end 176 of the sleeve 170 includes a plurality of fingers 178 which flex radially inward as the distal end 176 is received within the channel 164.

One of the fingers 178 may include a protrusion 179 extending laterally therefrom so that, when the protrusion 179 is received within the recess 168 of the channel 164, the fingers 178 revert to their initial configuration so that the fingers 178 "snap" into position within the channel 164. The rod 172 is sized and shaped to be received within the sleeve 170 so that, when the rod is 172 is moved distally relative to the sleeve 170 so that the rod 172 is received between the plurality of fingers 178, the fingers 178 are locked in an engaged configuration within the channel 164 and are prevented from being inadvertently disengage therefrom. In another embodiment, the fingers 178 may be biased toward a radially inward position so that moving the rod 172 so that the rod 172 is received between the fingers 178 moves the fingers 178 radially outward so that the protrusion 179 engages the recess 168. It will be understood by those of skill in the art that the terms proximal and distal as used herein to described portions of the insertion device 124, are intended to refer to a direction toward (proximal) and away (distal) from the surgeon or other user of the device.

When it is desired to assemble the fixation clamp 101 for insertion about a bone, the locking nut 118 is positioned over the first opening 116 of the first clamp member 102 so that the distal end 176 of the sleeve 170 is inserted first through the locking nut 118, then through the opening 116 so that the distal end 176 may engage the channel 164 of the stud 114, as described above. Once the distal end 176 of the insertion device 124 is fixed relative to the second clamp member 104 by moving the rod 172 distally within the sleeve 170 to move the plurality of fingers 178 radially outward, the first clamp member 102 is permitted to be slid proximally along the sleeve 170, until the surface 182 of the locking nut 118 abuts a stop 196 at the proximal end 174 of the sleeve 170. The first clamp member 102 is movable along the sleeve 170 while the second clamp member 104 is rigidly fixed to the sleeve 170 and the rod 172, the rod 172 being threaded into the second clamp member 104.

When the first clamp member 102 is drawn proximally so that the locking nut 118 abuts the stop 196, second ends 108, 112 of the first and second clamp members 102, 104 are separated from one another via a distance greater than a width of the bone (e.g., a maximum distance between a medial side of the bone and a lateral side of the bone) so that the fixation clamp 101 may be slid over the bone into a position about the hone. Once the fixation clamp 101 has been positioned about the bone, the first clamp member 102 and the locking nut 118 may be moved distally along the insertion device 124 so that the locking nut 118 may be threaded over the threaded portion 160 of the stud 114. The rod 172 is drawn proximally relative to the sleeve 170 so that the plurality of fingers 178 revert to their biased configuration and the distal end 176 of the sleeve 170 is disengaged from the stud 114 so that the insertion device 124 may be removed from fixation clamp 101. As described above, the locking nut 118 is tightened over the threaded portion 160 to draw the first and second clamp members 102, 104 closed toward one another, thereby fixing the fixation clamp 101 over the bone.

It will be understood by those of skill in the art that widths of bones may vary from patient to patient. Thus, a variety of sizes of fixation clamps 101 may be available so that a suitable fixation clamp may be selected based on the width of the patient bone. In one embodiment, a length of the stud 114 of the fixation clamp 101 is selected to correspond to the width of the bone of the patient being treated. It will be understood by those of skill in the art that a size and curvature of the first and second clamp members 102, 104 may also vary depending on a size of the bone being treated.

Figure 12:
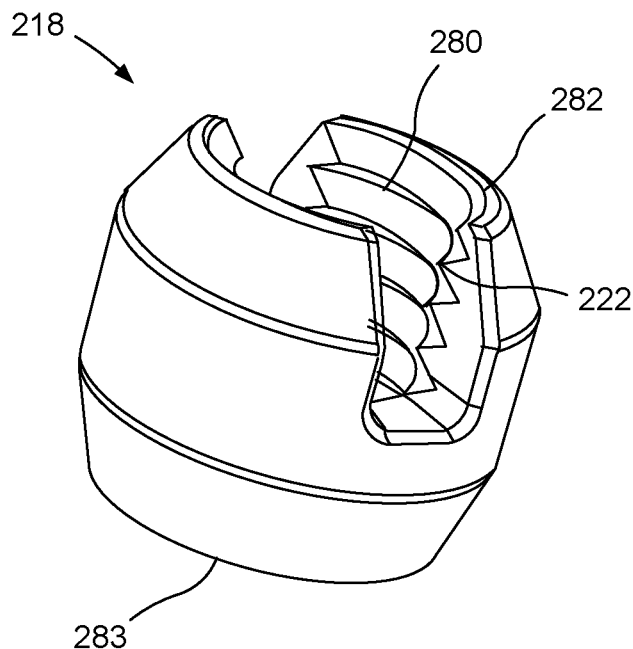
FIG. 12 shows a perspective view of a locking nut according to another exemplary embodiment of the present disclosure.
Figure 13:
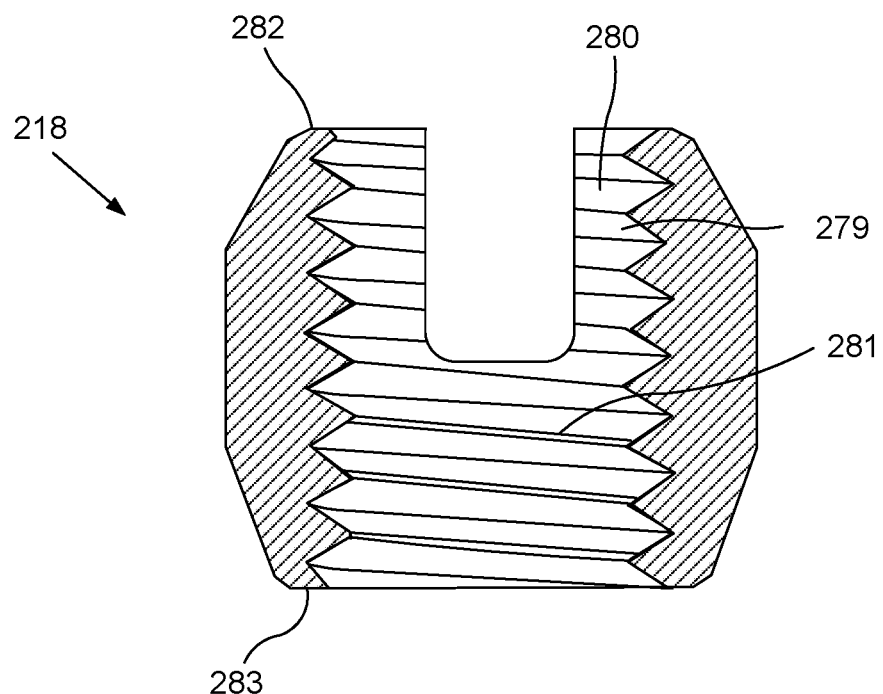
FIG. 13 shows a cross-sectional view of the locking nut of FIG. 12.

As shown in FIGS. 12-13, a locking nut 218 according to another exemplary embodiment may be used in the system 100, as described above, in place the locking nut 118. The locking nut 218 is substantially similar to the locking nut 118, including a threaded channel 280, via which the locking nut 218 threadedly engages the threaded portion 160 of the stud 114, and an anti-loosening feature 222 which engages the threaded portion 160 in such a manner as to prevent a post-operative loosening relative thereto.

Rather than a deformable portion as described with the respect to the locking nut 118, however, the anti-loosening feature 222 is configured as a reduced minor diameter along a first portion 279 of the threaded channel 280 extending from a first surface 282 of the locking nut 218 which, in an operative configuration, faces away from the second clamp member 204, relative to a second portion 281 of the threaded channel 280, which extends from the first portion 279 to a second surface 283 opposing the first surface 282. The minor diameter is defined via radially innermost edges of the threaded channel 280.

In one example, the minor diameter of the first portion 279 may be approximately 4.8 mm while the minor diameter of the second portion 281 may be approximately 5.0 mm. It will be understood by those of skill in the art, however, that the minor diameter of the first and second portions 279, 281 of the threaded channel 280 may have any of a variety of configurations so long as the minor diameter of the first portion 279 is smaller than the diameter of the second portion 281. In one embodiment, the first portion 279 extends along four turns of threading of the threaded channel 280 so a transition in the minor diameter occurs after four turns from the first surface 282. It will be understood by those of skill in the art that the reduced minor diameter along the first portion 279 provides increased friction with the threads of the stud 114 received therein to prevent backing out (e.g., loosening) of the locking nut 218 relative to the stud 114 of the fixation clamp 101.

As shown in FIGS. 14-16, a fixation clamp 301 according to another exemplary embodiment may be substantially similar to the fixation clamp 101, as described above with respect to the system 100, including a first clamp member 302 and a second clamp member 304 that are couplable relative to one another to extend about and engage a long bone. Rather than a locking nut and stud, however, the fixation clamp 301 further includes a shoulder bolt 314 for coupling the first and second clamp members 302, 304.

The first clamp member 302 is substantially similar to the first clamp member 302, extending from a first end 306 to a second end 308 along a curve corresponding to, for example, a lateral surface of the bone. Similarly to the first clamp member 102, the first clamp member 302 includes an opening 316 extending through the first end 306 for coupling the first clamp member 302 to the second clamp member 304. The second clamp member 304 is substantially similar to the second clamp member 104, extending from a first end 310 to a second end 312 along a curve corresponding to, for example, a medial surface of the bone. The first end 310, however, does not include a stud extending therefrom. Rather, the first end 310 include a threaded opening 318 extending therethrough for threadedly engaging a threaded portion 360 of the shoulder bolt 314.

The threaded opening 318 includes an anti-loosening feature 322 which prevents a post-operative loosening of the shoulder bolt 314. In one embodiment, the anti-loosening feature 322 is configured as a deformable portion 388 which deforms to cause an interference between threads of the shoulder bolt 314 and threads of the opening 318. In one example, the deformable portion 388 is defined via a first slit 390 and a second slit 394 extending through a wall of the opening 318. In one embodiment, the first slit 390 extends through the wall, from a first end 317 of the opening 318 toward a second end 319 of the opening 318, to an end 392. The second slit 394 extends from the end 392 of the first slit 390, about a portion of a circumference of the opening 318.

The shoulder bolt 314 includes the threaded portion 360 connected to a shoulder 315 via an unthreaded portion 362. To coupled the first and second clamp members 302, 304, the threaded portion is inserted through the opening 316 of the first clamp member 302 and into the threaded opening 318 of the second clamp member 304 so that threaded portion 360 threadedly engages the threaded opening 318. In particular, when the first and second clamp members 302, 304 are positioned about the bone in a desired position, axes of the openings 316, 318 are substantially coaxially aligned so that the shoulder bolt 314 may be inserted thereinto along the axes thereof.

The shoulder bolt 314 may be inserted through the openings 316, 318 until the shoulder 315 abuts a surface of the opening 316 of the first clamp member 302. Thus, as the shoulder bolt 314 is tightened (e.g., rotated relative to the first and second clamp members 302, 304), engagement between the threaded portion 360 and the threaded opening 318 causes the first and second clamp members 302, 304 to be drawn toward one another until the first and second clamp members 302, 304 are compressed about the bone. As the threaded portion 360 of the shoulder bolt 314 is driven through the threaded opening 318, the deformable portion 388 is deformed, causing an interference with threads of the threaded portion 360 of the shoulder bolt 314 and substantially locking (e.g., preventing loosening) of the shoulder bolt 314 relative to the second clamp member 304.

It will be apparent to those skilled in the art that various modifications and variations can be made in the structure and the methodology of the present invention, without departing from the spirit or the scope of the invention. Thus, it is intended that the present invention cover the modifications and the variations of this invention provided that they come within the scope of the appended claims and their equivalents.

What is claimed is:

1. A bone fixation clamp, comprising:
    a first clamp member extending from a first end to a second end along a curve corresponding to an outer surface along a first target portion of a bone, the first end including an opening extending therethrough along an axis which, when the first clamp member is positioned along the first target portion in an operative configuration, extends adjacent to the bone;
    a second clamp member extending from a first end to a second end along a curve corresponding to an outer surface along a second target portion of the bone;
    a stud extending longitudinally from the first end of the second clamp member to a free end so that, when the second clamp member is positioned along the second target portion of the bone in the operative configuration, the stud is receivable within the opening of the first clamp member along the axis of the opening; and
    a locking nut including a threaded channel configured to threadedly engage a portion of the stud so that, when the first and second clamp members are in the operative configuration, the locking nut is threadable over the stud to fix the first and second clamp members over the bone, the locking nut including an anti-loosening feature which, when the locking nut is threaded over the stud, results in an interference with threading along the stud,
    wherein the anti-loosening feature includes a deformable portion deforming to interfere with threading along the stud,
    wherein the locking nut extends longitudinally from a first end to a second end, the locking nut including a pair of grooves extending into the first end, through a wall of the locking nut so that the threaded channel is open to an exterior of the locking nut via the pair of grooves, and
    wherein the deformable portion is defined via a first slit extending through the wall of the locking nut from a first one of the pair of grooves about a portion of a circumference of the locking nut and a second slit extending through the wall of the locking nut from an end of the first slit toward the first end of the locking nut.

2. The bone fixation clamp of claim 1, wherein the pair of grooves are substantially diametrically positioned relative to one another.

3. The bone fixation clamp of claim 1, wherein the stud and the opening of the first clamp member are correspondingly sized and shaped so that the stud is non-rotatably receivable within the opening.

4. The bone fixation clamp of claim 1, wherein the stud includes a flat along a length thereof and the opening of the first clamp member includes a corresponding flat surface therealong.

5. The bone fixation clamp of claim 1, wherein a length of the stud is selected to correspond to a width of a bone being treated.

6. The bone fixation clamp of claim 1, wherein the second clamp member includes an elongated slot extending therealong and therethrough from a bone-facing surface of the second clamp member which, when the second clamp member is in the operative configuration faces toward a bone, to a surface of the second clamp member opposing the bone-facing surface of the second clamp member.

7. The bone fixation clamp of claim 6, wherein the elongated slot is open at the second end of the second clamp member to define a pair of prongs of the second clamp member.

8. The bone fixation clamp of claim 7, wherein the second clamp member includes a connecting web connecting the pair of prongs along a portion of the elongated slot.

9. The bone fixation clamp of claim 1, wherein the first clamp member includes a groove extending therealong, the groove sized and shaped to correspond to a bone plate so that, the first clamp member is mountable over a portion of a bone along which a bone plate is positioned.

10. The bone fixation clamp of claim 9, wherein a portion of the first clamp member including the groove includes a connecting opening extending therethrough so that, when the connecting opening is aligned with a corresponding hole of a bone plate over which the first clamp member is mounted, a screw is insertable through the connecting opening and the hole of the plate to fix the first clamp member and the bone plate relative to one another.

11. The fixation clamp of claim 1, wherein, when the locking nut threadedly engages the portion of the stud, the locking nut is at least partially snuggly surrounded by the first clamp member.

12. A bone fixation system, comprising:
a clamp including a first clamp member and a second clamp member, the first clamp member extending from a first end to a second end along a curve corresponding to an outer surface along a lateral side of a bone, the first end including an opening extending therethrough along an axis which, when the first clamp is positioned along the bone in an operative configuration, extends adjacent to the bone, the second clamp member extending from a first end to a second end along a curve corresponding to an outer surface along a medial side of the bone, a stud extending longitudinally from the first end of the second clamp member to a free end so that, when the second clamp member is positioned along the second target portion of the bone in the operative configuration, the stud is receivable within the opening of the first clamp member along the axis of the opening, the stud including a channel at the free end thereof;
a locking nut including a threaded channel configured to threadedly engage a portion of the stud so that, when the first and second clamp members are in the operative configuration, the locking nut is threadable over the stud to fix the first and second clamp members over the bone, the locking nut including an anti-loosening feature which, when the locking nut is threaded over the stud, results in an interference with threading along the stud; and
an insertion device including a sleeve extending from a proximal end to a distal end and sized and shaped to be slidable insertable through the threaded channel of the locking nut and the opening of the first clamp member, the distal end configured to engage the channel of the stud and the proximal end configured to engage the opening of the first clamp member so that, when the distal end of the sleeve engages the stud and the proximal end of the sleeve engages the first clamp member, second ends of the first and second clamp members are separated from one another by a distance greater than a width of the bone so that the fixation clamp is positionable about the bone.

13. The bone fixation system of claim 12, wherein the channel of the stud includes a recess extending along a portion thereof.

14. The bone fixation system of claim 13, wherein the distal end of the sleeve includes a plurality of fingers, one of the fingers including a protrusion extending laterally therefrom, the protrusion configured to be received within the recess of the stud so that the distal end of the sleeve engages the channel of the stud via a snap fit.

15. The bone fixation system of claim 11, wherein the insertion device includes a rod longitudinally slidable within the sleeve, the rod movable between a locking position, in which the rod is received between the fingers to lock the protrusion within the recess and the sleeve relative to the second clamp member, and an unlocked configuration, in which the rod is moved proximally relative to the sleeve so that the fingers are permitted to move radially inward relative to one another to disengage the sleeve from the channel of the stud.

16. The bone fixation system of claim 12, wherein the proximal end of the sleeve includes a stop for engaging the first clamp member.

17. The bone fixation system of claim 12, wherein the anti-loosening feature includes a deformable portion deforming to interfere with threading along the stud, the deformable portion defined via slits extending through a wall of the locking nut.

18. The bone fixation system of claim 12, wherein the anti-loosening feature includes a reduced minor diameter along a first portion of the threaded channel relative to a minor diameter along a second portion of the threaded channel.

19. A bone fixation clamp, comprising:
a first clamp member extending from a first end to a second end along a curve corresponding to an outer surface along a first target portion of a bone, the first end including a first opening extending therethrough along an axis which, when the first clamp is positioned along the first target portion in an operative configuration, extends adjacent to the bone;
a second clamp member extending from a first end to a second end along a curve corresponding to an outer surface along a second target portion of the bone, the first end of the second clamp member including a second opening extending therethrough along an axis so that, in the operative configuration, axes of the first and second openings are substantially coaxially aligned, the second opening including a threading therealong, the second opening including a deformable portion; and
a shoulder bolt configured to fix the first and second clamp members relative to one another over a bone, the shoulder bolt including a shoulder and a shaft sized and shaped to be slidably inserted through the first opening, a portion of the shaft including a threading for engaging the thread of the second opening, the deformable portion deforming to interfere with the threading of the shaft, wherein a threaded portion of the shaft of the shoulder bolt is connected to the shoulder via an unthreaded portion;
wherein the deformable portion is defined via slits extending through a wall of the second opening.

20. The fixation clamp of claim 19, wherein the shoulder is configured to engage a portion of the first opening so that, when the shoulder abuts the first opening and the shoulder bolt is tightened relative to the second clamp member, the first and second clamp members are drawn toward one another.

21. A bone fixation clamp, comprising:
a first clamp member extending from a first end to a second end along a curve corresponding to an outer surface along a first target portion of a bone, the first end including an opening extending therethrough along an axis which, when the first clamp member is positioned along the first target portion in an operative configuration, extends adjacent to the bone;
a second clamp member extending from a first end to a second end along a curve corresponding to an outer surface along a second target portion of the bone;

a stud extending longitudinally from the first end of the second clamp member to a free end so that, when the second clamp member is positioned along the second target portion of the bone in the operative configuration, the stud is receivable within the opening of the first clamp member along the axis of the opening;

a locking nut including a threaded channel configured to threadedly engage a portion of the stud so that, when the first and second clamp members are in the operative configuration, the locking nut is threadable over the stud to fix the first and second clamp members over the bone; and a tab coupled to the second end of the first clamp, the tab including a first bone fixation element receiving hole extending therethrough and being coupled to the second end of the first clamp via a bending zone.

22. The fixation clamp of claim 21, wherein the locking nut including an anti-loosening feature which, when the locking nut is threaded over the stud, results in an interference with threading along the stud, the locking nut extending longitudinally from a first end to a second end, the locking nut including a pair of grooves extending into the first end, through a wall of the locking nut so that the threaded channel is open to an exterior of the locking nut via the pair of grooves, wherein a deformable portion is defined via a first slit extending through the wall of the locking nut from a first one of the pair of grooves about a portion of a circumference of the locking nut and a second slit extending through the wall of the locking nut from an end of the first slit toward the first end of the locking nut.

\* \* \* \* \*